United States Patent
Utley et al.

(10) Patent No.: US 11,653,878 B2
(45) Date of Patent: May 23, 2023

(54) SYSTEMS AND METHODS FOR QUANTIFICATION OF, AND PREDICTION OF SMOKING BEHAVIOR

(71) Applicant: Carrot Sense, Inc., San Carlos, CA (US)

(72) Inventors: David S. Utley, Redwood City, CA (US); Jack D. Utley, Fairview, PA (US); Kathryn M. Utley, Redwood City, CA (US); Alek D. Utley, Redwood City, CA (US); Haley G. Utley, Redwood City, CA (US); MacKenzie T. Utley, Redwood City, CA (US); Emma K. Utley, Redwood City, CA (US)

(73) Assignee: Pivot Health Technologies Inc., San Carlos, CA (US)

( * ) Notice: Subject to any disclaimer, the term of this patent is extended or adjusted under 35 U.S.C. 154(b) by 0 days.

(21) Appl. No.: 15/213,265

(22) Filed: Jul. 18, 2016

(65) Prior Publication Data
US 2016/0324469 A1 Nov. 10, 2016

Related U.S. Application Data

(63) Continuation of application No. 14/537,070, filed on Nov. 10, 2014, now Pat. No. 9,420,971, which is a
(Continued)

(51) Int. Cl.
*A61B 5/00* (2006.01)
*A24F 47/00* (2020.01)
(Continued)

(52) U.S. Cl.
CPC ............ *A61B 5/4848* (2013.01); *A24F 47/00* (2013.01); *A61B 5/082* (2013.01); *A61B 5/1455* (2013.01);
(Continued)

(58) Field of Classification Search
CPC ........ G16H 50/20; G16H 50/30; G16H 80/00; A61B 5/082; A61B 5/4845; A61B 5/486;
(Continued)

(56) References Cited

U.S. PATENT DOCUMENTS

| | | |
|---|---|---|
| 3,953,566 A | 4/1976 | Gore |
| 4,220,142 A | 9/1980 | Rosen et al. |

(Continued)

FOREIGN PATENT DOCUMENTS

| | | |
|---|---|---|
| CN | 107708584 | 2/2018 |
| GB | 2379509 | 3/2003 |

(Continued)

OTHER PUBLICATIONS

Piasecki, Thomas M., Alison E. Richardson, and Shawn M. Smith. "Self-monitored motives for smoking among college students." Psychology of Addictive Behaviors 21.3 (2007): 328 (Year: 2007).*

(Continued)

*Primary Examiner* — Christopher A Flory
(74) *Attorney, Agent, or Firm* — Levine Bagade Han LLP

(57) ABSTRACT

Devices, methods and systems are disclosed for assisting patients in behavioral modification and cessation programs aimed at terminating undesired behaviors such as smoking, alcohol use and others. Patient devices configured to be easily carried or worn including test units such as carbon monoxide blood level sensors with automated patient prompting for self-testing, analysis of test results and data logging are included in a networked system with a specifically designed treatment modality. Devices and methods disclosed are particularly suited to use in smoking cessation treatment and programs.

22 Claims, 2 Drawing Sheets

Related U.S. Application Data continuation-in-part of application No. 12/910,371, filed on Oct. 22, 2010, now Pat. No. 9,675,275.

(60) Provisional application No. 61/902,646, filed on Nov. 11, 2013, provisional application No. 61/254,685, filed on Oct. 24, 2009.

(51) Int. Cl.

| | | |
|---|---|---|
| A61B 5/08 | (2006.01) | |
| A61B 5/145 | (2006.01) | |
| A61B 5/1455 | (2006.01) | |
| G16H 50/20 | (2018.01) | |
| G16H 10/20 | (2018.01) | |
| G16H 20/70 | (2018.01) | |
| G16Z 99/00 | (2019.01) | |
| A61B 5/1171 | (2016.01) | |
| A61B 5/1477 | (2006.01) | |

(52) U.S. Cl.
CPC ...... *A61B 5/14507* (2013.01); *A61B 5/14551* (2013.01); *A61B 5/486* (2013.01); *A61B 5/4845* (2013.01); *A61B 5/6801* (2013.01); *A61B 5/7475* (2013.01); *G16H 10/20* (2018.01); *G16H 20/70* (2018.01); *G16H 50/20* (2018.01); *G16Z 99/00* (2019.02); *A61B 5/0059* (2013.01); *A61B 5/1171* (2016.02); *A61B 5/1477* (2013.01); *A61B 5/4833* (2013.01); *A61B 5/742* (2013.01)

(58) Field of Classification Search
CPC .............. A61B 5/14551; A61B 5/4848; A61B 5/6801; A61B 5/742; A61B 5/7475
See application file for complete search history.

(56) References Cited

U.S. PATENT DOCUMENTS

| | | | |
|---|---|---|---|
| 4,246,913 A | 1/1981 | Ogden et al. | |
| 4,277,452 A | 7/1981 | Kanehori et al. | |
| 4,585,417 A | 4/1986 | Sozio et al. | |
| 4,609,349 A | 9/1986 | Cain | |
| 4,615,681 A * | 10/1986 | Schwarz | A24F 15/005 |
| | | | 131/270 |
| 4,629,424 A | 12/1986 | Lauks et al. | |
| 4,853,854 A | 8/1989 | Behar et al. | |
| 4,896,143 A | 1/1990 | Dolnick et al. | |
| 4,904,520 A | 2/1990 | Dumas et al. | |
| 4,971,558 A | 11/1990 | Jacobi | |
| 4,992,049 A | 2/1991 | Weissman | |
| 4,996,161 A | 2/1991 | Conners et al. | |
| 5,021,457 A * | 6/1991 | Akin | A61K 9/0056 |
| | | | 514/653 |
| 5,035,860 A | 7/1991 | Kleingeld et al. | |
| 5,063,164 A | 11/1991 | Goldstein | |
| 5,188,109 A | 2/1993 | Saito | |
| 5,284,163 A | 2/1994 | Knudsen et al. | |
| 5,293,875 A | 3/1994 | Stone | |
| 5,361,771 A | 11/1994 | Craine et al. | |
| 5,565,152 A | 10/1996 | Od et al. | |
| 5,596,994 A * | 1/1997 | Bro | G06F 19/3456 |
| | | | 600/545 |
| 5,618,493 A | 4/1997 | Goldstein et al. | |
| 5,647,345 A | 7/1997 | Saul | |
| 5,764,150 A | 6/1998 | Fleury et al. | |
| 5,778,897 A | 7/1998 | Nordlicht | |
| 5,826,577 A | 10/1998 | Perroz, Jr. et al. | |
| 5,829,971 A | 11/1998 | Razdolsky et al. | |
| 5,841,021 A | 11/1998 | De et al. | |
| 5,908,301 A | 6/1999 | Lutz | |
| 6,039,688 A | 3/2000 | Douglas et al. | |
| 6,067,523 A | 5/2000 | Bair et al. | |
| 6,164,278 A | 12/2000 | Nissani | |
| 6,334,778 B1 * | 1/2002 | Brown | G16H 10/20 |
| | | | 434/258 |
| 6,340,588 B1 | 1/2002 | Nova et al. | |
| 6,397,093 B1 | 5/2002 | Aldrich | |
| 6,544,199 B1 | 4/2003 | Morris | |
| 6,599,253 B1 | 4/2003 | Smits et al. | |
| 6,544,190 B1 | 7/2003 | Baum et al. | |
| 6,602,892 B1 | 8/2003 | Sachs | |
| 6,613,001 B1 | 9/2003 | Dworkin | |
| 6,730,494 B1 | 5/2004 | Toranto et al. | |
| 6,748,792 B1 | 6/2004 | Freund et al. | |
| 6,858,182 B1 | 2/2005 | Ito et al. | |
| 7,054,679 B2 | 5/2006 | Hirsh | |
| 7,163,511 B2 | 1/2007 | Conn et al. | |
| 7,408,640 B2 | 8/2008 | Cullum et al. | |
| 7,421,882 B2 | 9/2008 | Leddy et al. | |
| 7,451,852 B2 | 11/2008 | Stewart et al. | |
| 7,525,093 B2 | 4/2009 | Stenberg | |
| 7,610,919 B2 | 11/2009 | Utley et al. | |
| 7,661,955 B2 | 2/2010 | Da | |
| 7,716,383 B2 | 5/2010 | Lei et al. | |
| 7,720,516 B2 | 5/2010 | Chin et al. | |
| 7,797,982 B2 | 9/2010 | Burke et al. | |
| 7,899,518 B2 | 3/2011 | Trepagnier et al. | |
| 8,130,105 B2 | 3/2012 | Al-Ali et al. | |
| 8,160,279 B2 | 4/2012 | Abolfathi | |
| 8,190,223 B2 | 5/2012 | Al-Ali et al. | |
| 8,211,035 B2 | 7/2012 | Melker et al. | |
| 8,224,411 B2 | 7/2012 | Al-Ali et al. | |
| 8,224,667 B2 | 7/2012 | Miller et al. | |
| 8,235,921 B2 | 8/2012 | Rousso et al. | |
| 8,249,311 B2 | 8/2012 | Endo et al. | |
| 8,311,601 B2 | 11/2012 | Besko | |
| 8,560,032 B2 | 10/2013 | Al-Ali et al. | |
| 9,420,971 B2 | 8/2016 | Utley et al. | |
| 9,675,275 B2 | 6/2017 | Utley et al. | |
| 9,861,126 B2 | 1/2018 | Utley et al. | |
| 10,206,572 B1 | 2/2019 | Utley et al. | |
| 10,335,032 B2 | 7/2019 | Utley et al. | |
| 10,499,819 B2 | 12/2019 | Wondka et al. | |
| 10,674,761 B2 | 6/2020 | Utley et al. | |
| 10,674,913 B2 | 6/2020 | Utley et al. | |
| 10,861,595 B2 | 12/2020 | Satake et al. | |
| 10,923,220 B2 | 2/2021 | Satake | |
| 11,257,583 B2 | 2/2022 | Chancellor et al. | |
| 11,278,203 B2 | 3/2022 | Utley et al. | |
| 11,412,784 B2 | 8/2022 | Utley et al. | |
| 2001/0027384 A1 | 10/2001 | Schulze et al. | |
| 2001/0027794 A1 | 10/2001 | Brue | |
| 2001/0037070 A1 | 11/2001 | Cranley et al. | |
| 2002/0026937 A1 * | 3/2002 | Mault | G01N 33/497 |
| | | | 128/200.24 |
| 2002/0061495 A1 | 5/2002 | Mault | |
| 2002/0072959 A1 | 6/2002 | Clendonon | |
| 2002/0146346 A1 | 10/2002 | Konecke | |
| 2002/0177232 A1 | 11/2002 | Melker et al. | |
| 2003/0003113 A1 | 1/2003 | Lewandowski | |
| 2003/0004403 A1 | 1/2003 | Drinan et al. | |
| 2003/0004426 A1 | 1/2003 | Melker et al. | |
| 2003/0015019 A1 | 1/2003 | O'Brien | |
| 2003/0050567 A1 | 3/2003 | Baghdassarian | |
| 2003/0109795 A1 | 6/2003 | Webber | |
| 2003/0149372 A1 | 8/2003 | Smith et al. | |
| 2003/0211007 A1 | 11/2003 | Maus et al. | |
| 2004/0006113 A1 | 1/2004 | Sachs | |
| 2004/0031498 A1 | 2/2004 | Brue | |
| 2004/0035183 A1 | 2/2004 | O'Brien et al. | |
| 2004/0158194 A1 | 8/2004 | Wolff et al. | |
| 2004/0210154 A1 | 10/2004 | Kline | |
| 2004/0239510 A1 | 12/2004 | Karsten | |
| 2005/0053523 A1 | 3/2005 | Brooke | |
| 2005/0081601 A1 | 4/2005 | Lawson | |
| 2005/0112148 A1 | 5/2005 | Dmitruk | |
| 2005/0141346 A1 | 6/2005 | Rawls et al. | |
| 2005/0163293 A1 | 7/2005 | Hawthorne et al. | |
| 2005/0171816 A1 | 8/2005 | Meinert et al. | |
| 2005/0177050 A1 | 8/2005 | Cohen | |
| 2005/0177056 A1 | 8/2005 | Giron et al. | |
| 2005/0177615 A1 | 8/2005 | Hawthorne et al. | |

(56) References Cited

U.S. PATENT DOCUMENTS

| | | | |
|---|---|---|---|
| 2005/0263160 A1* | 12/2005 | Utley | A24F 47/00 |
| | | | 131/270 |
| 2006/0144126 A1 | 7/2006 | O'Brien et al. | |
| 2006/0167723 A1 | 7/2006 | Berg | |
| 2006/0193749 A1 | 8/2006 | Ghazarian et al. | |
| 2006/0220881 A1 | 10/2006 | Al et al. | |
| 2006/0226992 A1 | 10/2006 | Al et al. | |
| 2006/0229914 A1 | 10/2006 | Armstrong | |
| 2006/0237253 A1 | 10/2006 | Mobley et al. | |
| 2006/0238358 A1 | 10/2006 | Al et al. | |
| 2007/0005988 A1 | 1/2007 | Zhang et al. | |
| 2007/0093725 A1* | 4/2007 | Shaw | G01N 33/4972 |
| | | | 600/543 |
| 2007/0164220 A1 | 7/2007 | Luk | |
| 2007/0168501 A1 | 7/2007 | Cobb et al. | |
| 2007/0209669 A1 | 9/2007 | Derchak | |
| 2007/0271997 A1 | 11/2007 | O'Brien | |
| 2007/0277823 A1 | 12/2007 | Al Ali et al. | |
| 2007/0277836 A1 | 12/2007 | Longley | |
| 2007/0282226 A1* | 12/2007 | Longley | A61F 5/566 |
| | | | 600/587 |
| 2007/0282930 A1 | 12/2007 | Doss et al. | |
| 2008/0078232 A1 | 4/2008 | Burke et al. | |
| 2008/0126277 A1* | 5/2008 | Williams | G06F 19/3481 |
| | | | 706/14 |
| 2008/0146890 A1 | 6/2008 | LeBoeuf et al. | |
| 2008/0162352 A1 | 7/2008 | Gizewski | |
| 2008/0199838 A1 | 8/2008 | Flanagan | |
| 2008/0221418 A1 | 9/2008 | Al-Ali et al. | |
| 2009/0069642 A1 | 3/2009 | Gao et al. | |
| 2009/0164141 A1 | 6/2009 | Lee | |
| 2009/0191523 A2 | 7/2009 | Flanagan | |
| 2009/0216132 A1 | 8/2009 | Orbach | |
| 2009/0253220 A1 | 10/2009 | Banerjee | |
| 2009/0293589 A1 | 12/2009 | Freund et al. | |
| 2009/0325639 A1 | 12/2009 | Koehn | |
| 2010/0009324 A1 | 1/2010 | Owens et al. | |
| 2010/0010321 A1 | 1/2010 | Foster | |
| 2010/0010325 A1 | 1/2010 | Ridder et al. | |
| 2010/0010433 A1 | 1/2010 | Krogh et al. | |
| 2010/0012417 A1 | 1/2010 | Walter et al. | |
| 2010/0081955 A1 | 4/2010 | Wood et al. | |
| 2010/0116021 A1 | 5/2010 | O'Brien | |
| 2010/0204600 A1 | 8/2010 | Crucilla | |
| 2010/0209897 A1 | 8/2010 | Utley et al. | |
| 2010/0234064 A1 | 9/2010 | Harris | |
| 2010/0280821 A1 | 11/2010 | Tiitola | |
| 2010/0298683 A1 | 11/2010 | Cabrera et al. | |
| 2011/0035158 A1 | 2/2011 | Banos et al. | |
| 2011/0079073 A1 | 4/2011 | Keays | |
| 2011/0125063 A1 | 5/2011 | Shalon et al. | |
| 2011/0153223 A1 | 6/2011 | Gentala et al. | |
| 2011/0247638 A1 | 10/2011 | Ayala | |
| 2011/0263947 A1 | 10/2011 | Utley et al. | |
| 2011/0265552 A1 | 11/2011 | Stedman | |
| 2011/0270052 A1 | 11/2011 | Jensen et al. | |
| 2011/0270053 A1 | 11/2011 | Utley et al. | |
| 2011/0295140 A1 | 12/2011 | Zaidi et al. | |
| 2012/0022890 A1 | 1/2012 | Williams et al. | |
| 2012/0068848 A1 | 3/2012 | Campbell et al. | |
| 2012/0115115 A1 | 5/2012 | Rapoza | |
| 2012/0130584 A1 | 5/2012 | Stedman | |
| 2012/0161970 A1 | 6/2012 | Al-Ali et al. | |
| 2012/0190955 A1 | 7/2012 | Rao et al. | |
| 2012/0191052 A1 | 7/2012 | Rao | |
| 2012/0232359 A1 | 9/2012 | Al-Ali et al. | |
| 2012/0238834 A1 | 9/2012 | Hornick | |
| 2012/0294876 A1 | 11/2012 | Zimmerman | |
| 2013/0211291 A1 | 8/2013 | Tran | |
| 2013/0233052 A1 | 9/2013 | Stedman | |
| 2013/0253849 A1 | 9/2013 | Gentala et al. | |
| 2013/0304581 A1 | 11/2013 | Soroca et al. | |
| 2013/0316926 A1 | 11/2013 | Caffrey | |
| 2014/0033796 A1 | 2/2014 | Stedman | |
| 2014/0051043 A1 | 2/2014 | Mosby | |
| 2014/0142965 A1 | 5/2014 | Houston et al. | |
| 2014/0228699 A1 | 8/2014 | Causevic et al. | |
| 2014/0257127 A1 | 9/2014 | Smith et al. | |
| 2014/0358018 A1 | 12/2014 | Neagle, III | |
| 2015/0024355 A1 | 1/2015 | Ghofrani et al. | |
| 2015/0025407 A1 | 1/2015 | Eichler et al. | |
| 2015/0032019 A1 | 1/2015 | Acker et al. | |
| 2015/0064672 A1 | 3/2015 | Bars | |
| 2015/0065825 A1 | 3/2015 | Utley et al. | |
| 2015/0201865 A1 | 7/2015 | Forzani et al. | |
| 2016/0029693 A1 | 2/2016 | Klein et al. | |
| 2016/0151603 A1 | 6/2016 | Shouldice et al. | |
| 2016/0192880 A9 | 7/2016 | Utley et al. | |
| 2016/0219931 A1 | 8/2016 | Doshi et al. | |
| 2016/0224752 A1 | 8/2016 | Van Wyck et al. | |
| 2016/0246936 A1 | 8/2016 | Kahn | |
| 2017/0055572 A1 | 3/2017 | Utley et al. | |
| 2017/0055573 A1 | 3/2017 | Utley et al. | |
| 2017/0319105 A1 | 11/2017 | Utley et al. | |
| 2017/0323065 A1 | 11/2017 | Proctor Beauchamp et al. | |
| 2018/0116560 A1 | 5/2018 | Quinn et al. | |
| 2018/0129535 A1 | 5/2018 | Carteri et al. | |
| 2018/0301214 A1 | 10/2018 | Satake et al. | |
| 2019/0104938 A1 | 4/2019 | Utley et al. | |
| 2019/0113501 A1 | 4/2019 | Jameson et al. | |
| 2019/0150831 A1 | 5/2019 | Payton et al. | |
| 2019/0239564 A1 | 8/2019 | Utley et al. | |
| 2019/0244015 A1 | 8/2019 | Lee | |
| 2019/0261855 A1 | 8/2019 | Utley et al. | |
| 2020/0288785 A1 | 9/2020 | Utley et al. | |
| 2020/0288979 A1 | 9/2020 | Utley et al. | |
| 2020/0305729 A1 | 10/2020 | Wondka et al. | |
| 2020/0342352 A1 | 10/2020 | Neumann | |
| 2021/0004377 A1 | 1/2021 | Neumann | |
| 2021/0057066 A1 | 2/2021 | Satake et al. | |
| 2021/0004691 A1 | 7/2021 | Neumann | |
| 2021/0196147 A1 | 7/2021 | Jameson et al. | |
| 2021/0202066 A1 | 7/2021 | Chancellor et al. | |
| 2022/0133400 A1 | 5/2022 | Chancellor et al. | |
| 2022/0233075 A1 | 7/2022 | Utley et al. | |

FOREIGN PATENT DOCUMENTS

| | | |
|---|---|---|
| JP | 2005-070953 | 3/2005 |
| JP | 2005070953 A * | 3/2005 |
| JP | 2018-503733 | 2/2018 |
| JP | 2018-517913 | 7/2018 |
| WO | WO 1994/000831 | 1/1994 |
| WO | WO 2005/117621 | 12/2005 |
| WO | WO 2006/118654 | 11/2006 |
| WO | WO 2016/164484 | 10/2016 |
| WO | WO 2019/074942 | 4/2019 |
| WO | WO 2021/138193 | 7/2021 |
| WO | WO 2021/138195 | 7/2021 |
| WO | WO 2021/138464 | 7/2021 |

OTHER PUBLICATIONS

Harsanyi, G. "Chemical Sensors for Biomedical Applications," *Biomedical Sensor*, Chapter 7, pp. 323-326, 2010.

McMillan, A.S. et al., "Reflex inhibition in single motor units of the human lateral pterygoid muscle," *Experimental Brain Research*, 76: 97-102, 1989, Department of Oral Biology, University of British Columbia.

Navy Cyanide Test Kit (NACTEK), http://www.nrl.navy.mil/research/nrl-review/2004/chemical-biochemical-researchl deschamps/, accessed Oct. 26, 2010.

Sung et. al., "Wearable feedback systems for rehabilitation," *Journal of NeuroEngineering and Rehabilitation*, 2:17, pp. 1-12, 2005.

Varshney, U. "Wireless Health Monitoring: Requirements and Examples," Pervasive Healthcare Computing: EMRI EHR, Chapter 5, pp. 89-118, Spring Science+Business LLC publishing, 2009.

Wu et. al., "MEDIC: Medical embedded device for individualized care," *Artificial Intelligence in Medicine*, 42, pp. 137-152, 2008.

Exhaled Breath Analysis: from Occupation to Respiratory Medicine, 2005.

(56) References Cited

OTHER PUBLICATIONS

Henningfield, J.E. et al., "Expired air carbon monoxide accumulation and elimination as a function of number of cigarettes smoked," *Addictive Behaviors*, vol. 5, No. 3, pp. 265-272, Jan. 1, 1980.
Smokerlyzer Justification Guide, 2010.
Deveci, S. E. et al. "The Measurement of Exhaled Carbon Monoxide in Healthy Smokers and Non-smokers," *Respiratory Medicine*, vol. 98, No. 6, pp. 551-556, Jun. 2004.
Jarvis, M. J. et al. "Comparison of Tests Used to Distinguish Smokers from Nonsmokers," *American Journal of Public Health*, vol. 77, No. 11, Nov. 1987.

\* cited by examiner

SYSTEMS AND METHODS FOR QUANTIFICATION OF, AND PREDICTION OF SMOKING BEHAVIOR

RELATED APPLICATION DATA

This application is a continuation of U.S. patent application Ser. No. 14/537,070 filed Nov. 10, 2014 (now U.S. Pat. No. 9,420,971), which claims the benefit of priority to U.S. Prov. Pat. App. 61/902,646 filed Nov. 11, 2013, and is a continuation-in-part of U.S. patent application Ser. No. 12/910,371 filed Oct. 22, 2010, which claims the benefit of priority of U.S. Prov. Pat. App. 61/254,685 filed Oct. 24, 2009. Each of the forgoing applications is incorporated by reference herein in its entirety.

FIELD OF THE INVENTION

The present invention generally relates to the field of behavioral modification. In particular, exemplary embodiments of the present invention are directed to extracorporeal devices, systems and methods for facilitating cessation of undesired behaviors.

BACKGROUND

Certain persons may engage in certain undesirable activities that have significant negative acute and/or long-term health, social, and safety implications for the person and for other associated persons. In some cases, the person may wish to quit this behavior. Often, the person's family, friends, and/or healthcare providers are also engaging with the person in an attempt to have them quit the behavior. Associated persons may also be negatively impacted by the behavior, socially, financially, and from a health perspective. Such behavioral modification or cessation attempts to terminate the undesirable behavior may be formal and administered by healthcare professionals, or the person may take their own personalized approach to cessation.

An example of such a behavioral modification program is a formal multi-modality smoking cessation program that utilizes counseling and drug therapy to achieve the end goal of abstinence from smoking. Drug therapy typically includes one or more of: nicotine replacement therapy, welbutryn, varenicline, and other drugs. Alcohol cessation programs, by comparison, may include similar approaches with counseling and drug interventions targeted specifically to achieve abstinence from alcohol use and abuse.

In a typical multi-modality smoking cessation program, participants are asked to voluntarily and honestly report on their smoking behavior before and during therapy. For example, the patient's baseline smoking behavior is measured according to the patient's own voluntary report and is based solely on their recall (i.e., patient states that they average forty cigarettes per day prior to entering program). The patient may also be asked to provide a blood sample at the clinic or hospital location to test for substances associated with smoking behavior, such as hemoglobin bound to carbon monoxide. Alternatively, the patient may be asked to exhale into a device at the clinic or hospital location to detect carbon monoxide levels in the exhaled gas from the lungs. Such tests would be performed on location and observed by the health care provider, and such tests may require processing by a professional laboratory. Based on the values of carbon monoxide or other substances at this specific point in time, a gross estimate of smoking behavior may be made by the health care professional. Limitations of such testing are that it is made at a single point in time and likely does not fully and accurately reflect the true behavior of the patient at multiple time points before entering the program. The patient may alter their behavior, for example, for days prior to testing thus making the test result less relevant and accurate.

At each visit during a patient's cessation program participation, the patient's interval smoking behavior since the previous visit is quantified by patient voluntary reporting (recollection, diary, etc.). For example, if the patient is seen weekly, they will report on their smoking behavior for the prior seven days. Typically, the patient keeps a diary or smoking log during each interval in which daily entries are made regarding the number of cigarettes smoked and certain lifestyle events that occur in conjunction with smoking behavior. This methodology relies on compliance and full disclosure by the smoker, as well as a commitment to record the data every day.

Clinical trials have shown that patients often fail to disclose their true smoking behavior when queried in this manner, grossly under-reporting the amount of smoking that takes place or forgetting certain lifestyle events that are associated with smoking. These limitations in reporting impair the effectiveness of the program. Further, blood tests or exhaled carbon monoxide breath tests may be performed on the spot at these weekly or biweekly visits, to detect substances associated with smoking. Unfortunately, such predictable and infrequent testing gives the patient the opportunity to abstain for hours or longer prior to the visit to avoid detection of smoking behavior or to lessen the positivity of the test. Such behavior results in collecting physiological data that erroneously suggests that smoking has stopped or diminished. For example, if a patient has a bi-weekly 3 pm clinic visit on Mondays, they may abstain from smoking after 9 am on the day of the visit so that their blood and exhaled breath levels of carbon monoxide decline or normalize in time for the test. Further, such spot testing by the clinic is infrequent and does not accurately represent patient behavior during non-clinic days. Due to these significant limitations, counseling and drug therapy cannot be accurately and effectively tailored to optimize patient outcomes. If healthcare professionals do not have accurate information regarding true patient behavior, for example, the efficacy of the cessation program will be severely impaired. This is one reason why failures of smoking cessation programs, as well as other behavioral cessation programs, are so high and recidivism almost guaranteed. Given the currently limited options for objectively determining a patient's smoking behavior, (or other behaviors) a more objective and accurate means of determining a patient's behavior is needed.

SUMMARY OF THE DISCLOSURE

In one exemplary embodiment of the present invention, a method for facilitating cessation of undesired behavior in a patient includes steps such as configuring a patient device with a predetermined test protocol including patient test prompts, prompting the patient in accordance with the predetermined test protocol to provide at least one biological input to the patient device, the biological input being correlated to the undesired behavior, analyzing the patient biological input to the patient device, generating a machine readable data set representative of the patient input based on the analyzing, associating the data set with a specific patient biological input, evaluating the predetermined test protocol based on the data set, and altering or maintaining the predetermined test protocol based on the evaluation. In certain embodiments, such a method may also include steps of determining whether the patient properly provided a biological input in response to the prompting, and re-prompting the patient to provide the at least one biological input when the determining result is negative.

Other aspects of exemplary embodiments may include remotely reconfiguring the test protocol in the patient device through a communications network, prompting the patient to input requested information to the patient device through a user interface, and associating the requested information with the data set associated with a specific patient's biological input. Additionally, the evaluating may be based on the requested information associated with the data set. In general, embodiments of the present invention will utilize at least a biological input, that is, an input from the patient that indicates or corresponds to a biological or medical condition of the patient. Other inputs, such as informational inputs, comprising information about patient environment, activities or state of mind, etc. may be utilized.

In further exemplary embodiments, methods according to the present invention may include transmitting the data set and associated requested information to a health care provider device. Other optional steps may include communicating with the patient device through a network, and prompting the patient to provide at least one biological input outside of the predetermined test protocol. In order to arrive at a test protocol, exemplary embodiments may also include collecting data related to the patient undesired behavior, and analyzing the patient behavior data to determine the predetermined test protocol.

In another exemplary embodiment of the present invention, system for facilitating cessation of undesired behavior in a patient includes a patient device or PD and a health care provider device or HCPD that are configured to communicate with one another through a network or other known means of data transfer. The PD may be configured and dimensioned to be carried by the patient, may include a PD user interface, a test element configured to receive a biological input from the patient and output information representative of the content of the biological input, a PD storage module containing instructions for various functions including for a predetermined test protocol, and a PD execution module communicating with the user interface, the test element and the storage module, the PD execution module configured to execute instructions contained in said PD storage module.

In some embodiments, the test element comprises a detector configured to detect substances in exhaled breath. In other embodiments, the test element comprises a detector configured to detect substances in saliva. In still other embodiments, the test element comprises a light wavelength sensor configured to be placed in contact with the patient's skin.

The predetermined test protocol instructions may, for example, include prompting the patient through the user interface to provide a biological input to the test element at selected intervals, the timing and frequency of the patient prompts including modification of the intervals based on analysis of various patient inputs, determining the completeness of a biological input, and providing additional patient prompts based on the completeness determination.

In such exemplary embodiments, an HCPD may be configured to be accessed by a health care provider, and include an HCPD user interface, an HCPD storage module containing certain instructions and an HCPD execution module communicating with the user interface and storage module, the execution module configured to execute instructions contained in the HCPD storage module.

Instructions stored in the HCPD storage module may include instructions for displaying and manipulating information representative of the content of the biological input, and revising the predetermined test protocol based on at least one of user input and the information representative of the content of the biological input.

In certain other exemplary embodiments instructions for executing some functions may be stored in either the PD or HCPD storage modules and executed by the associated execution modules as appropriate. Examples of such instructions may include instructions for generating a machine readable data set based on the test element output information, and for associating the data set with a specific patient biological input, or instructions for causing the patient device to prompt the patient to input requested information to the patient device through the PD user input and for associating the requested information with a data set associated with a specific patient biological input.

In further exemplary embodiments, the patient device may further include an identification device for acquiring patient identifying information correlated to a biological input. Such an identification device may communicate with the storage module and execution module for associating the acquired identifying information with the correlated biological input and storing the associated identifying information. The system may also permit receiving unprompted patient input through the PD user input and then associating the unprompted input with a biological input based on a predetermined algorithm.

In another exemplary embodiment of the present invention, an apparatus for use in connection with facilitating cessation of undesired behavior in a patient, may include at least one housing configured and dimensioned to be carried by the patient, a user interface disposed in the at least one housing, a test element disposed in the at least one housing, the test element being configured to receive a biological input from the patient and output information representative of the content of the biological input, a storage module containing instructions related to the operation of the apparatus, and an execution module communicating with the user interface, the test element and the storage module.

Exemplary instructions contained in the storage model, which may be executed by the execution module, may include instructions for executing a predetermined test protocol, b) generating user readable indicator based on the test element output and displaying the output on the user interface, associating the user readable indicator with a specific biological input, associating the requested information with a specific user readable indicator associated with a specific patient biological input, and storing test result information including the user readable indicator and associated requested information in the storage module. The predetermined test protocol instructions may include steps of prompting the patient through the user interface to provide a biological input to the test element at selected intervals, determining the completeness of a biological input, providing additional patient biological input prompts based on the completeness determination, and prompting the patient to input requested information through the user interface.

In some exemplary embodiments, the apparatus may be configured to communicate through a network for transfer of the test result information.

In yet another exemplary embodiment of the present invention, a method for collecting and confirming patient participation in select behaviors, may include steps such as configuring a patient device with a predetermined test protocol including patient test prompts, prompting the patient in accordance with the predetermined test protocol to provide at least one biological input to the patient device, the biological input being correlated to the select behavior, determining whether the patient properly provided a biological input in response to the prompting, re-prompting the patient to provide the at least one biological input when the determining result is negative, analyzing the patient biological input to the patient device, generating a machine readable data set representative of the patient input based on the analyzing, associating the data set with a specific patient biological input, prompting the patient to input requested information to the patient device through a user interface, associating the requested information with the data set associated with a specific patient biological input, evaluating the predetermined test protocol based on the data set and the requested information associated with the data set.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
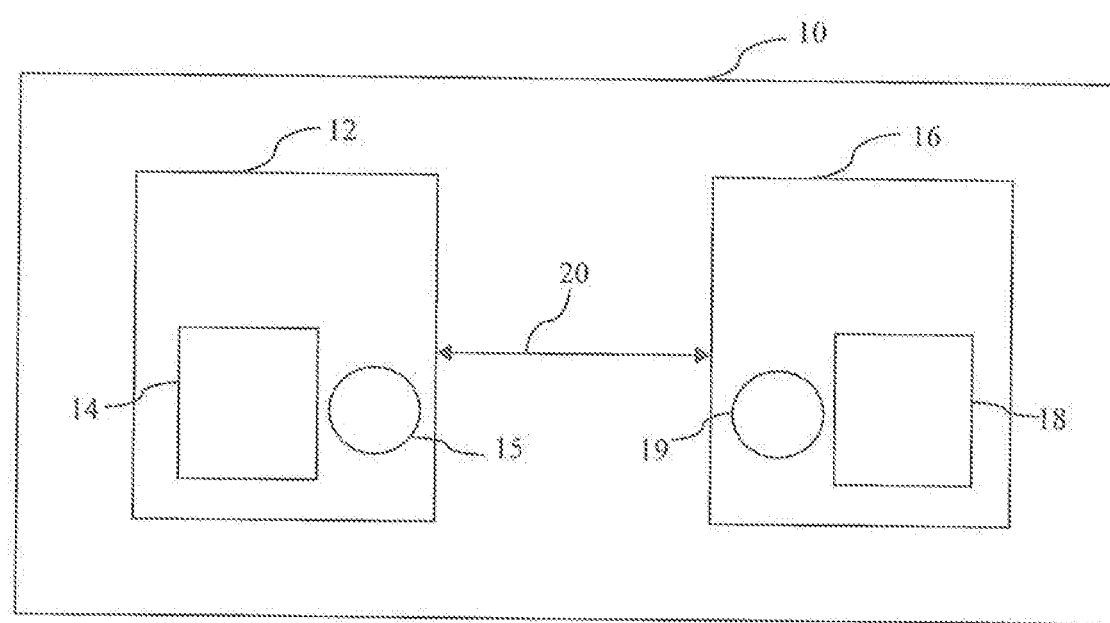
FIG. 1 is a block diagram illustrating a patient monitoring device according to an exemplary embodiment of the present invention.

Embodiments of the present invention provide devices, methods and systems capable of prompting a patient to perform self-testing for undesired behaviors, objectively analyzing the test results, logging the data to a local or central storage unit, and providing a comprehensive interface for the patient and healthcare professional to analyze and observe results and correlate these results with progress within a cessation program. Such self-testing may be according to a protocol that is monitored and altered in real time to adapt to specific circumstances of the patient's needs. While exemplary embodiments of the present invention are described in more detail in connection with smoking cessation, and to some extent alcohol cessation, it will be appreciated by those skilled in the art that the devices, methods and systems taught herein are generally applicable to facilitating behavior modification with respect to any number of undesired behaviors for which markers are present in the patient's blood, breath or saliva.

A number of undesirable behaviors that involve smoking of one or more substances, oral ingestion of one or more substances, oral placement of one or more substances, transdermal absorption of one or more substances, nasal sniffing of one or more substances, and other methods of absorbing one or more substances result in the subsequent presence of one or more of the substances in the blood and/or exhaled breath. The presence of a unique substance or substances can be used as a marker for the specific undesirable behavior and intermittent testing of the exhaled breath for this substance(s) can quantify the occurrence of the undesirable behavior.

Such substances may be detected in the exhaled breath due to one or more of the following mechanisms: 1) the substance was previously absorbed into the body and bloodstream and is then released from the bloodstream into the pulmonary airspace for exhalation, 2) the substance was very recently inhaled into the pulmonary dead space (non-absorbing portion of inhaled air) and is being exhaled acutely therefore not requiring a blood level of the substance to be present, 3) the substance is present in the oral cavity mucous and epithelial surface layers and certain portions volatilized into the exhaled breath, 4) the substance was previously absorbed into the body and bloodstream and is then released from salivary glands into the oral cavity in the saliva and then volatilized into the exhaled breath, and/or 5) the substance was exhaled previously and a portion of the substance was retained within the oral cavity mucous and epithelial surface layers and certain portions subsequently volatilized into the exhaled breath.

One alternative to intermittently testing the exhaled breath to detect one or more substances associated with an undesirable behavior is to intermittently test saliva for one or more substances associated with an undesirable behavior, as these substances as disclosed above often reside in the oral cavity via secretion within the saliva from the bloodstream or accumulation within the oral cavity mucous, saliva, and epithelial lining due to ingestion or exhalation residues.

Another alternative testing mode is based on measurement of light passing through patient tissue and analysis of attenuation of various wavelengths. Such light-light based test modes may be implemented with finger clips, bands or adhesively-applied sensor pads. As will be understood by persons skilled in the art, examples include different types of PPG (photoplethysmogram) sensing. One example is transmissive PPG sensors such as pulse oximeters. In such sensors, at least two waveforms of light are transmitted through the skin and a sensor/receiver on the other side of the target (e.g., the finger) analyzes the received waveforms to determine the sensor result. In another example, carbon monoxide content in blood may be sensed by determining levels of carboxyhemoglobin in the blood. Sensors for carboxyhemoglobin may transmit and sense more than two light waveforms. Another suitable type of PPG sensing is reflectance PPG wherein light is shined against the target, and the receiver/sensor picks up reflected light to determine the measurement of the parameter of interest.

In the specific example of smoking cessation, high quality objective data collected in an improved manner could be used by the healthcare professional to adjust therapy (i.e., nicotine replacement therapy, other drug therapy, counseling, etc.) to achieve a better outcome, to provide real-time or delayed positive and negative feedback to the patient, to determine success or failure of the cessation program, and to provide long-term maintenance of cessation after successfully quitting the behavior (avoidance of recidivism). For example, if smoking behavior remained unchanged after initiating counseling and a trial of nicotine replacement therapy (NRT), the dose of the NRT could be immediately increased and/or other therapies could be added with this approach. Likewise, as smoking behavior began to improve as evidenced by objective signs of decreased frequency of smoking, the various therapies could be titrated downward and ultimately discontinued.

An exemplary embodiment of a patient monitoring device according to the present invention is illustrated in FIG. 1. In this exemplary embodiment, patient device 10 includes two main components: extra-corporeal detector unit 12 containing at least one test element and signaling unit 16. The components may be combined into a single unit or may be separated physically. Other embodiments may include additional components and these components may be combined or separate as well.

Extra-corporeal detector unit 12 includes at least one test element that is capable of detecting a substance using an input of a biological parameter from the patient that is indicative of recent targeted behavior. The detector analyzes the biological input from the patient, such as expired gas from the lungs or saliva or wavelengths of light directed through or reflected by tissue, and in at least one embodiment logs the date and time of day, quantifies the presence of the targeted substance(s), and then stores the data for future analysis and/or sends the data to a remote location for analysis. Detector unit 12 thus may include a processor, memory and user interface 14 as appropriate for its specific functions. The user interface may include data inputs such as a touch screen, keyboard or pointer.

Detector units may be specifically configured by person of ordinary skill in the art for detection of specific marker substances related to targeted behaviors as described herein. Examples of substances detected related to smoking include but are not limited to carbon monoxide, nitrogen oxides, ammonia, arsenic, nicotine, acetone, acetaldehyde, formaldehyde, hydrogen cyanide, isoprene, methyl ethyl ketone, benzene, toluene, phenol, and acrylonitrile. Sensor technologies for detecting alcohol in the exhaled breath include infrared spectrophotometer technology, electrochemical fuel cell technology, or a combination of the two. Smaller portable units well suited for use in embodiments of the invention may be based on electrochemical fuel cell analysis or "Taguchi cell" sensors.

One example of a suitable detector unit for determining the presence of alcohol in the breath is described in U.S. Pat. No. 7,797,982, entitled "Personal Breathalyzer Having Digital Circuitry." Another example of detector units that may be configured to determine the presence of a variety of substances is disclosed in U.S. Pat. No. 7,421,882, entitled "Breath-based Sensors for Non-invasive Molecular Detection." U.S. Pat. No. 7,525,093, entitled "Liquid or Gas Sensor and Method" discloses another sensor device that may be readily incorporated into embodiments of the present invention by persons of ordinary skill in the art. Each of the forgoing U.S. patents are incorporated by reference herein in their entirety.

Examples of other detector units include sensors for transcutaneous or transmucosal detection of blood carbon monoxide (CO) levels. Such sensors are capable on non-invasively determining blood CO levels and other parameters based on analysis of the attenuation of light signals passing through tissue. Examples of such sensors are disclosed in U.S. Pat. No. 8,224,411, entitled "Noninvasive Multi-Parameter Patient Monitor." Another example of a suitable sensor is disclosed in U.S. Pat. No. 8,311,601, entitled "Reflectance and/or Transmissive Pulse Oximeter". Each of these two U.S. Patents are incorporated by reference herein in their entirety, including all materials incorporated by reference therein.

Detector unit 12 may also be configured to recognize a unique characteristic of the patient, such as a fingerprint, retinal scan, voice label or other biometric identifier, in order to prevent, at least to a degree, having a surrogate respond to the signaling and test prompts to defeat the system. For this purpose, patient identification sub-unit 15 may be included in detector unit 12. Persons of ordinary skill in the art may configure identification sub-unit 15 as needed to include one or more of a fingerprint scanner, retinal scanner, voice analyzer, or face recognition as are known in the art. Examples of suitable identification sub-units are disclosed, for example in U.S. Pat. No. 7,716,383, entitled "Flash-interfaced Fingerprint Sensor," and U.S. Patent Application Publication No. 2007/0005988, entitled "Multimodal Authentication," each of which is incorporated by reference herein in their entirety.

Identification sub-unit 15 may also comprise a built in still or video camera, which would record a picture or video of the patient automatically as the biological input is provided to the test element. Regardless of the type of identification protocol used, the processor and memory in the detector unit will associate the identification with the specific biological input, for example by time reference, and may store that information along with other information regarding that specific biological input for later analysis.

A patient may also attempt to defeat the detector by blowing into the detector with a pump, bladder, billows, or other device, for example, when testing exhaled breath. In the embodiment of saliva testing, a patient may attempt to substitute a "clean" liquid such as water. For light-based sensors, the patient may ask a friend to stand in for him or her. While no means will absolutely prevent an uncooperative and determined patient from these attempts, some means to defeat these attempts can be incorporated into the system. For example, the detector unit may incorporate the capability of discerning between real and simulated breath delivery. In one exemplary embodiment this functionality may be incorporated by configuring detector unit 12 to sense oxygen and carbon dioxide, as well as the maker substance (carbon monoxide, etc.). In this manner, the detector is able to confirm that the gas being analyzed is truly coming from expired breath, as expired breath has lower oxygen and much higher carbon dioxide than ambient air. In another embodiment, the detector unit may be additionally configured to detect enzymes naturally occurring in saliva so as to distinguish between saliva and other liquids. Basic biochemical tests are well known to persons skilled in the art for identifying such substances. Light-based sensors can be used to measure blood chemistry parameters other than CO levels and thus results may be compared to known samples representing the patient's blood chemistry.

Signaling unit 16 may communicate with detector unit 12 through an appropriate communication link 20 (for example, wired, WI-FI, Bluetooth, RF, or other means) as may be devised by a person of ordinary skill in the art based on the particular application. Signaling unit 16 may be integrated with detector unit 12 in patient device 10 or may separate from the detector unit, but the units are synchronized and able to communicate real-time or at various intervals in order to correlate signaling and detector results. Thus, when physically separate from detector unit 12, signaling unit 16 may include its own processor, memory and graphical user interface 18, but when integrated with detector unit 12 both units may share one of more of those subcomponents. Utilizing graphical user interface 18, signaling unit 16 prompts the patient to provide the required input(s) to the detector unit at various times of the day as appropriate for the specific detector unit and sensor modality. For breath-based sensors, patient input may comprise blowing into a tube as part of the detector unit. For saliva or other body fluid-based sensors, patient input may comprise placement of a fluid sample in a test chamber provided in the detector unit. For light-based sensors, patient input may comprise placement of an emitter-detector on a finger or other area of exposed skin. Together, memory for detector unit 12 and signaling unit 16 will contain instructions appropriate for operation of the patient device in accordance with the various method embodiments described herein.

In some circumstances, a prompt to test may have to be ignored for reasons not considered noncompliant due to the patient being engaged in an activity that prevents testing, such as exercise, work, driving, etc. A means by which to delay testing in response to a prompt, such as "snooze button" 19 may be incorporated. For example, if a patient is driving a vehicle, they may push button 19 to activate a preset interval until the test is again requested. A certain number of delays may be permitted each day, with this number being set by the provider or patient in the program.

Signaling unit 16 may also include means permitting the patient to input information that the patient believes relevant to his or her condition without prompting. Such information may, for example, include information about the patient's state of mind, that is feeling stressed or anxious. Such unprompted information could then be correlated to a biological input based on a predetermined algorithm, such as being associated with the biological input that is closest in time to the unprompted input, or associated with the first biological input occurring after the unprompted input.

In one exemplary embodiment of patient device 10, detector and signaling units 12, 16 are combined and exist in an entirely portable configuration with battery power. Such embodiments may also be provided with network connection capability (WI-FI, wireless cell, RF, etc.) as described in greater detail below. For example, a PDA-like device that is able to both signal the patient as well as perform the expired gas analysis could be carried in the patient's pocket at all times and improve compliance by the patient by allowing them to respond immediately to notifications.

In yet another exemplary embodiment, wherein detector unit 12 and signaling unit 16 are physically separate units, the signaling unit may be configured to be worn as a wristwatch or carried like a PDA. Likewise, the detector would be worn or carried, but separately. In any separate unit embodiment, the units are time synchronized or linked via a wireless communication link 20 to allow analysis of the time dependent data (linking of the notification and exhalation events).

Figure 2:
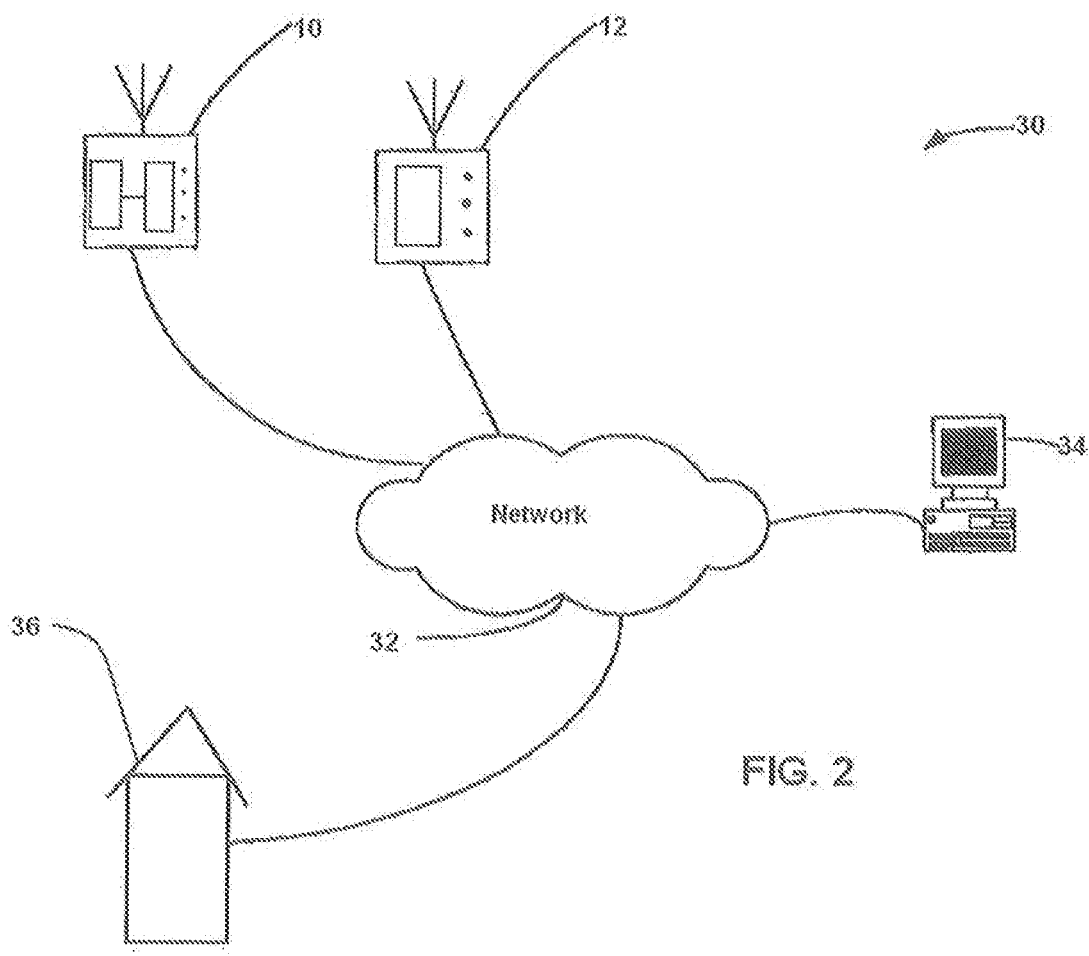
FIG. 2 is a diagram illustrating a system according to an exemplary embodiment of the present invention.

In the example of a combined unit or wirelessly (or wired) connected units, either the detector or the signaling unit could act as the storage entity for the data utilizing its own internal memory. Alternatively, either could act as the sending unit to upload the data to a remote source for live tracking of patient data as described in more detail below. Data could be uploaded immediately, intermittently or not at all. The data could also be downloaded from the storage media either by the patient or health care professional In a further exemplary embodiment, as illustrated in FIG. 2, system 30 includes mobile patient devices 10 (including integrated detector and signaling units) and/or stand alone detector units 12 that communicate through network 32 with healthcare provider base station 34. Network 32 may comprise the Internet, a land-based or cellular telephone network or any other communications networks or combination of networks as appropriate for the particular patients and cessation program. Healthcare provider base station 34 may comprise a specially programmed personal computer in a doctor's office linked to communication network 32 through a7n appropriate communications buss or a specialized device including its own memory, processor and graphical user interface. Persons of ordinary skill in the art may configure and program base station 34 based on the teachings contained herein.

System 30 also may include fixed patient devices 36. Fixed patient devices may comprise substantially the same components as mobile patient devices 10 except that they are configured to be fixed at a particular location such as a patient's home, office or automobile. In addition, system 30 permits remote programming by the healthcare provider as appropriate for the particular patient and/or cessation program. An exemplary method for implantation of a cessation program utilizing system 30 is described in greater detail with reference to the flow chart of FIG. 3.

Figure 3:
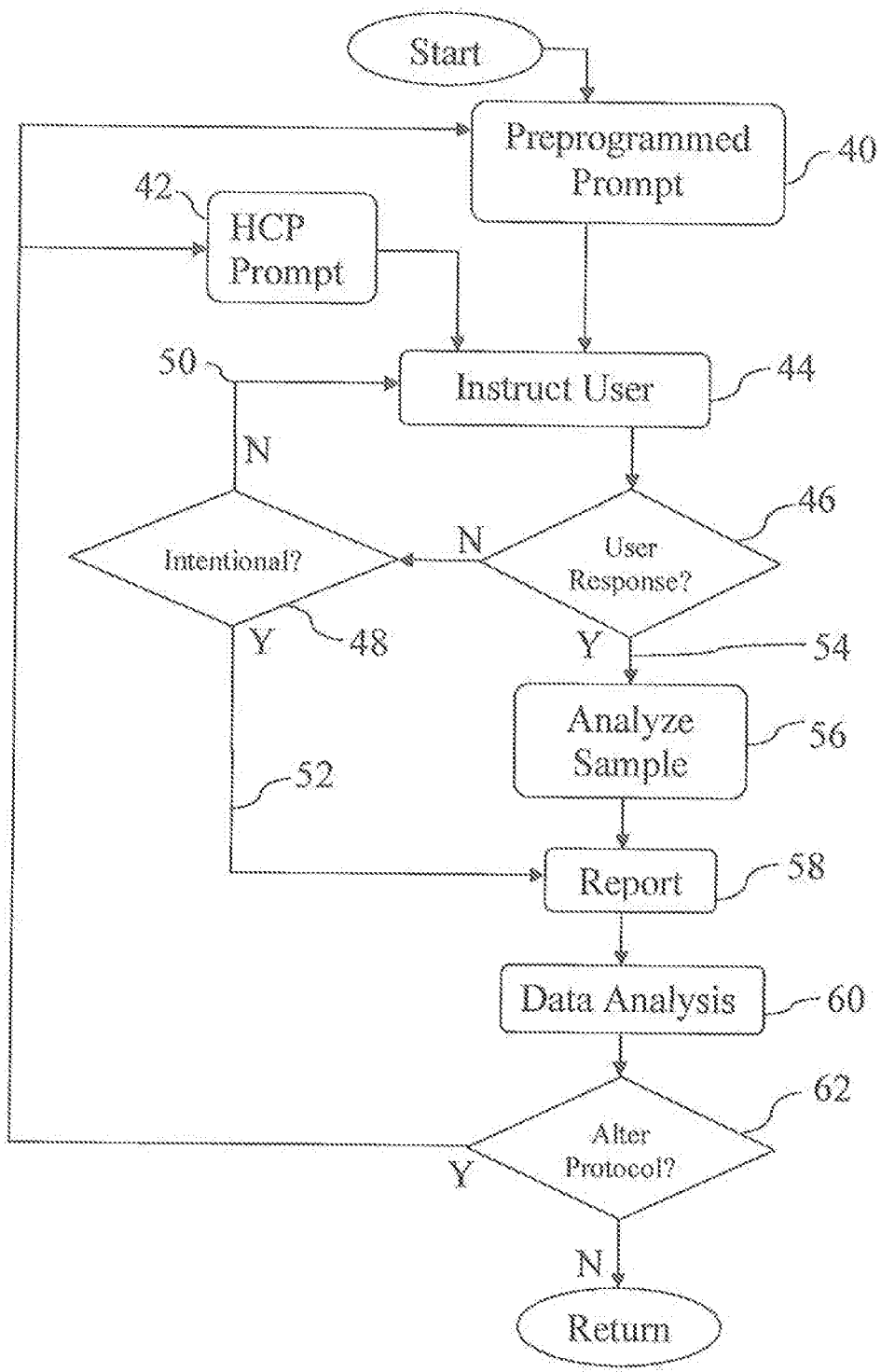
FIG. 3 is a flow chart illustrating a method according to an exemplary embodiment of the present invention.

As illustrated in FIG. 3, system 30 may be preprogrammed to prompt the patient at specific times (step 40) and/or the healthcare provider (HCP) may randomly prompt the patient (step 42) when there is a concern that behavior is timed to avoid preprogrammed prompts. Alternatively the programmed prompts 40 may occur at random intervals as described in more detail below. For example, patient devices 10 may be programmed to be operational during prescribed hours (typically waking hours, for example from 6 am to 11 pm), although sleep hour function can be activated. The patient is prompted at various times throughout the day to exhale into the detector. The patient is instructed (step 44) with each prompt regarding how to properly and consistency perform the requested test. In one example of an algorithm for breath testing, the patient will take several full breaths in and out into the detector, followed by a deep test exhalation for the detector to analyze. A determination is then made (step 46) as to whether the patient has complied. Circumstances of non-compliance may also be determined (step 48). For example if device 10 determines that there was simply no attempt at compliance the patient may be re-instructed a set number of times (branch 50). However, after a predetermined number of re-instructions without compliance, the device simply may report a non-compliant episode (branch 52). Alternatively, if it is determined that the patient attempted to comply but compliance was incomplete (for example, does not exhale fully) then the test may be rejected and the patient instructed to repeat the test (branch 50).

When compliance is determined (branch 54), the sample is analyzed (step 56) according to the predetermined detector unit protocol. Marker substances, if present, may be quantified at each test interval if such analysis is included in the protocol. Each event may be reported (step 58), either in real time through network communications or via periodic downloads. To facilitate reporting and data logging, data regarding the qualitative (yes/no) values as well as the quantitative substance level may be stored within the detector in a memory unit such as a flash drive or disk. Alternatively, as mentioned, the unit may upload the data live via a cell connection or local network. Such upload may occur intermittently or immediately. Disk space may be freed up upon confirmation of successful upload, as needed. Reported events are analyzed (step 60), for example by being categorized as either negative or positive for the substance of interest based on a pre-determined threshold for positivity, and therefore negative or positive for the smoking behavior. The threshold for positivity may be set at standard levels derived from the scientific literature or may be adjusted by the healthcare professional to the specific needs of the patient. Such adjustments may occur in real time 62 based on data analysis and may include changes in the testing as well as prompting protocols.

If the patient fails to respond (fails to blow into the unit or appropriately place the light emitter-detector) within a certain period of time after receiving the signal to respond (for example, within 3 minutes although the time interval allowable for testing may be set at any preferred value), the event is interpreted as a failure and flagged in the database. Data analysis can interpret failed tests as being positive for smoking behavior or may omit the value entirely. The analysis tool is capable of variably dealing with such failed signals for testing. If considered positive for a smoking behavior, a positive quantitative value may be assigned to that data point. Such a design prevents the patient from gaining a benefit (logging a negative data point) by ignoring a signal if they were engaging in smoking at the time of the signal to test.

Programming necessary to implement the exemplary methodology illustrated in FIG. 3 may exist entirely within software or firmware resident in patient device 10, divided between detector unit 12 and signaling unit 16 as appropriate for the particular configuration of the device. Alternatively, such programming may at least in part reside in a server or other source associated with base station 34, communicating with patient devices 10 and 36 and/or detector unit 12 through communications network 32.

Regardless of the exact embodiment of the invention as a single unit (combined and integrated) or multiple units, an advantage of the present invention is that it may be specifically configured for individual patients so that the detector and signaling unit can be with the patient at all times. The patient is thus able to respond to a signaling notification within the allotted and permitted time interval (i.e., within about 2-10 minutes) at all times and may not use lack of availability as an excuse for noncompliance.

In one exemplary embodiment, the patent prompts are programmed to be intermittent and of varying intervals, so as not to be predictable. The frequency of prompting can vary throughout the day, and the pattern can be unpredictable and non-repeating, thus preventing the patient from predicting when they will be notified to blow into the detector or test saliva. Alternatively, or additionally, the healthcare provider may initiate additional prompts through network 32 when in appropriate circumstances. This unpredictability and variability prevents the patient from modifying the timing of their smoking behavior in such a manner so as to avoid detection of the smoking behavior or to minimize the quantitative result of the test. Further, the number of signaling events per day can vary, for example on one day twenty signals may be delivered, while on the next day only twelve are delivered. Variability can be important, for example, if the signaling unit notified the patient every hour on the hour, the smoker could smoke three cigarettes immediately after the hour then avoid smoking for the remainder of the hour until prompted next. Presumably, during that hour-long interval of no smoking, the substance detected in expired gas or saliva might return to lower or even undetectable levels. To prevent the patient from predicting when the notification will occur, the notification schedule will be unpredictable and can be programmed in an infinite number of permutations based on frequency, number of notifications per day, max/min time between notifications, time allowed to respond, etc. Further, the pattern of notifications will not repeat itself on subsequent days, further making the pattern unpredictable and undefeatable.

Patient devices 10, 36 according to embodiments of the invention may be programmed to be active during wake hours only or may include sleep hours as well. In the former, the hours of operation are programmable based on healthcare provider choice and patient need. One example would be to have the unit active from 6 am to 12 midnight every day. Another example would be to have the unit be normally active during the waking hours with frequent notifications at unpredictable times, and then revert to an alternative schedule during sleep hours where only one or two signals occur at night. This would provide a modicum of aversion to smoking at night by the patient in an attempt to defeat the system, yet would not dramatically disrupt sleep patterns. Another alternative would be to have the system active twenty-four hours per day, and night time failed test events (no response by patient) be considered as sleep events and not counted against the patient as positive for the undesirable behavior.

EXAMPLE

The following is one example of a practical application of one embodiment of the invention. A patient is enrolled in a smoking cessation program and self-reports a certain amount of smoking behavior (number of cigarettes smoked per day) upon entry into the program (baseline smoking behavior). The patient completes the enrollment process and initial counseling visit with a healthcare professional. The patient begins NRT and is provided with mobile patient device 10 programmed to function between 6 am and 12 midnight each day. During the active daily interval, the signaling unit prompts the patient approximately twenty times each day to follow the provided instructions for how to perform exhalation testing with the detector unit. The detector unit may also provide displayed or audio instructions through the graphical user interface. The patient must comply within a predetermined time period (for example, within 3 minutes of notification) or else the event is considered a failure to respond. In the analysis of the data, this failure to respond can be treated as a positive smoking behavior event or can be ignored. In the example of carbon monoxide as the test substance, the level of CO (ppm) is recorded at each test instance. All data is logged and stored in the detector or signaling unit (or uploaded real time or intermittently) until downloaded to a software analysis program. Further, the user interface may prompt the patient to enter additional information about lifestyle events that occur during the day (meals, activity, sex, alcohol consumption, stress, travel, etc.) that can then be temporally correlated with smoking behavior as detected by the exhaled gas to draw conclusions about trigger events for smoking behavior. For example, after a test the detector unit may scroll through a number of potential scenarios for selection by the patient (i.e., did you have a meal in the last thirty minutes, did you have a drink in the last thirty minutes). If not uploaded automatically through a communications network, then at the one-week visit, the healthcare provider downloads the data and uses a software program to analyze the data. Alternatively, the data was uploaded in advance of the visit obviating the need for download. A print out is provided which shows the daily notification times and the associated CO levels, as well as the missed or possibly faked responses. The analysis program is described further below, but there are several summary metrics which could be tracked to estimate the number of cigarettes smoked and the timing of peak substance in the bloodstream. Correlations are made between program interventions versus trends in smoking behavior over time. Correlations are also made between recorded lifestyle events and smoking behavior to allow improved counseling and drug therapy interventions. The printed analysis is provided to the patient for positive/negative feedback regarding their progress and response to therapy. Each week, this process is repeated, progress towards the goal of smoking cessation is tracked and medical therapy is adjusted according to the objective data in an optimized manner.

Analysis of the data can be performed in many different ways in various alternative embodiments. Once the data is uploaded or downloaded, many different metrics can be summarized and analyzed. Each day of use may have, for example, twenty test points for analysis. The timing and number of test points is variable and can be preprogrammed according to healthcare professional recommendation and needs. Each test point will have a yes/no, binary value, as well as a quantitative value. The yes/no value may have a role in determining if the patient is smoking "at all" and, if any tests are "yes", may provide some insight into how often during the day the patient is smoking. The quantitative value for each test interval, if positive, may provide additional information about how often the patient is smoking and trends towards abstinence. Also these trends can provide information about peaks of smoking during each day and week. CO levels in expired gas, for example, peak immediately after smoking a cigarette or series of cigarettes, and then gradually decline over time. CO levels in blood show a different response. A time vs. CO level could be plotted and a predictive algorithm created to estimate the number of cigarettes and time of smoking per day for each patient. A time vs. CO level plot for each test period (day, week, month, year) provides significant information to the healthcare provider regarding patient progress in a longer term program and allows alteration of therapy in an objective manner. Further, on the time vs. CO plot, data regarding administration of medication, changes in medication regimens over time, counseling interventions, etc. can be annotated and used to track effect of each intervention and dose change. Such data analysis functionality may be incorporated into patient devices 10, 36, or may reside in healthcare provider base station 34.

Another software analysis feature involves an interactive program that the patient engages within the interval between cessation program visits (for example, between biweekly program visits). Such a patient-interface could be used by persons who independently utilize this cessation system outside of a smoking cessation program. While the devices would be similar to the previously disclosed detector and signaling units, such an embodiment may include means by which the patient can upload the data on a regular basis to a local or remote source (or both) and follow their data on a regular basis for trends and feedback. As the data is uploaded and analyzed, the data is added to previously uploaded data and can be viewed by the patient and healthcare provider and other authorized persons. The data can be displayed for any party in the same manner as it is displayed for the healthcare professional. Alternatively, unique, patient-friendly interactive displays can be provided for the patient so that they can track and observe their smoking behavior in a number of ways, including total number of days in the program, baseline smoking behavior compared to current smoking behavior, number of cigarettes avoided in last period of time, number of hours, days, months, and years of lifetime saved, time to goal of smoking cessation, daily results, weekly results, progress towards goal displayed numerically or graphically. Other metrics can also be tracked and correlated with smoking behavior results, such a blood pressure, heart rate, body weight, quality of life testing, stress level questionnaire results, and others. If viewed simultaneously by the qualified health care professional, prompts can be provided to the patient that are positive reinforcement about good behavior and improvements, alterations that may be made to drug therapy, observations about lifestyle events that may be precipitating smoking behavior, etc. Additionally, the patient can observe within the analysis program which lifestyle events may be impacting daily smoking behavior. Avoidance of these situations can then ensue.

In such a patient-centric interactive program, a series of questions could be levied each day (or more or less frequently) to the patient, which could be standardized or could be prompted by certain changes (improvement or worsening) in smoking behavior. For example, a patient may be asked at the end of each day to log in the analysis program the number of cigarettes smoked, blood pressure measurement, heart rate, quality of life scale questions, significant life event, etc. Results of these queries can be tracked overtime with the smoking behavior objective readings from the CO monitoring data. Such linkage of patient volunteered data as well as objective data and therapeutic intervention data are helpful for the patient and healthcare professional to tailor therapy optimally.

While exemplary embodiments of the invention are described above with a focus on smoking behaviors, examples of which include but are not limited to smoking of tobacco via cigarettes, pipes, cigars, and water pipes, and smoking of illegal products such as marijuana, cocaine, heroin, and alcohol related behaviors, it will be immediately apparent to those skilled in the art that the teachings of the present invention are equally applicable to any number of other undesired behaviors for which markers are present in the breath and/or saliva. Such other examples include: oral placement of certain substances, with specific examples including but not limited to placing chewing tobacco and snuff in the oral cavity, transdermal absorption of certain substances, with specific examples including but not limited to application on the skin of certain creams, ointments, gels, patches or other products that contain drugs of abuse, such as narcotics, and LSD, and nasal sniffing of drugs or substances of abuse, which includes but is not limited to sniffing cocaine. In general, the basic configuration of patient devices 10, 36, as well as the prompting, self-testing, data logging, feedback and other steps and methods as disclosed herein will be similar as between the different behaviors that are being addressed. However, detector unit 12 may differ somewhat in design only to account for different marker substances that are required for testing or different testing methodology necessitated by the different markers associated with particular undesired behaviors. For example, a light-based sensor may be worn and activated when prompted, rather than placed when prompted.

It will also be appreciated by persons of ordinary skill in the art that a patient participating in a formal cessation program may take advantage of the assistive devices, methods and systems disclosed herein as adjuncts to the cessation program. However, in alternative embodiments, it will be equally appreciated that the patient may be independently self-motivated and thus beneficially utilize the assistive devices, methods and systems for quitting the undesired behavior unilaterally, outside of a formal cessation program.

In further exemplary embodiments of the present invention, devices, systems and methods disclosed herein may be readily adapted to data collection and in particular to collection of reliable and verifiable data for studies related to undesired behaviors for which the present invention is well suited to test. Such studies may be accomplished with virtually no modification to the underlying device or methods except that where treatment was not included there would not necessarily be a need for updating of the test protocol or treatment protocol based on user inputs.

What is claimed is:

1. A method of quantifying an individual's smoking behavior, comprising:
    obtaining a plurality of samples of exhaled air from the individual over a period of time using a detector unit configured to be carried by the individual and recording a collection time associated with each sample of exhaled air;
    determining whether each of the samples is sufficiently compliant for measurement;
    measuring an amount of exhaled carbon monoxide for each of the samples of exhaled air determined to be compliant using a sensor in the detector unit;
    transmitting data relating to the amount of exhaled carbon monoxide and the collection time for each sample from the detector unit to a remote unit which is configured to be carried by the individual separately from the detector unit and which is synchronized with the detector unit;
    compiling a dataset comprising the amount of exhaled carbon monoxide and the collection time for each sample of exhaled air via the remote unit;
    identifying trends in a smoking behavior with respect to at least one peak of a carbon monoxide level measured from the samples of exhaled air over the period of time;
    quantifying an exposure of exhaled carbon monoxide over an interval of time within the period of time via the remote unit;
    determining progress of the individual towards an abstinence trend based on the carbon monoxide levels measured from the samples of exhaled air; and
    displaying the progress of the individual towards the abstinence trend.

2. The method of claim 1 further comprising displaying the trends that correlate exhaled carbon monoxide load with respect to the interval of time.

3. The method of claim 1 wherein obtaining a plurality of samples of exhaled air comprises sequentially obtaining the plurality of samples of exhaled air.

4. The method of claim 1 wherein obtaining a plurality of samples of exhaled air comprises generating a signal to the individual to provide at least one sample of exhaled air.

5. The method of claim 1 wherein obtaining a plurality of samples of exhaled air comprises alerting the individual on a repeating basis to provide the sample of exhaled air over the period of time.

6. The method of claim 1 where measuring an amount of exhaled carbon monoxide comprises using a portable sensor.

7. The method of claim 1 wherein quantifying an exposure of exhaled carbon monoxide comprises correlating a function of exhaled carbon monoxide versus time over the period of time using the dataset.

8. The method of claim 1 wherein receiving the input data from the individual further comprises recording a time of the input.

9. The method of claim 1 further comprising:
    determining a number of cigarettes avoided by the individual; and
    displaying the number of cigarettes avoided by the individual.

10. The method of claim 1 further comprising transmitting the amount of exhaled carbon monoxide and the collection time associated with each sample of exhaled air to an electronic device.

11. The method of claim 1 further comprising obtaining a result of a behavioral questionnaire from the individual and displaying the result of the behavioral questionnaire over the interval of time.

12. A method of quantifying an individual's smoking behavior, comprising:
    obtaining a plurality of samples of exhaled air from the individual over a period of time using a detector unit configured to be carried by the individual and recording a collection time associated with each sample of exhaled air;
    determining whether each of the samples is sufficiently compliant for measurement;
    measuring an amount of exhaled carbon monoxide for each of the samples of exhaled air determined to be compliant using a sensor on the detector unit;
    transmitting data relating to the amount of exhaled carbon monoxide and the collection time for each sample from the detector unit to a remote unit which is configured to be carried by the individual separately from the detector unit and which is synchronized with the detector unit;
    compiling a dataset comprising the amount of exhaled carbon monoxide and the collection time for each sample of exhaled air via the remote unit;
    correlating a function of an exposure of exhaled carbon monoxide over an interval of time using the dataset over the period of time via the remote unit;
    identifying trends in a smoking behavior with respect to at least one peak of a carbon monoxide level measured from the samples of exhaled air over the interval of time from the dataset;
    displaying the trends upon a display;
    determining progress of the individual towards an abstinence trend based on the carbon monoxide levels measured from the samples of exhaled air; and
    displaying the progress of the individual towards the abstinence trend.

13. The method of claim 12 further comprising displaying the trends that correlate exhaled carbon monoxide load with respect to the interval of time.

14. The method of claim 12 wherein obtaining a plurality of samples of exhaled air comprises sequentially obtaining the plurality of samples of exhaled air.

15. The method of claim 12 wherein obtaining a plurality of samples of exhaled air comprises generating a signal to the individual to provide at least one sample of exhaled air.

16. The method of claim 12 wherein obtaining a plurality of samples of exhaled air comprises alerting the individual on a repeating basis to provide the sample of exhaled air over the period of time.

17. The method of claim 12 where measuring an amount of exhaled carbon monoxide comprises using a portable sensor.

18. The method of claim 12 further comprising altering a therapy provided to the individual in response to identified trends from the dataset.

19. The method of claim 12 wherein receiving the input data from the individual further comprises recording a time of the input.

20. The method of claim 12 further comprising:
    determining a number of cigarettes avoided by the individual; and
    displaying the number of cigarettes avoided by the individual.

21. The method of claim 12 further comprising transmitting the amount of exhaled carbon monoxide and the collection time associated with each sample of exhaled air to an electronic device.

22. The method of claim 12 further comprising obtaining a result of a behavioral questionnaire from the individual and displaying the result of the behavioral questionnaire over the interval of time.

\* \* \* \* \*